US00PP29518P3

(12) United States Plant Patent
Stemkens

(10) Patent No.: US PP29,518 P3
(45) Date of Patent: Jul. 17, 2018

(54) ***VERBENA* PLANT NAMED 'VEAZ0043'**

(50) Latin Name: *Verbena hybrida*
Varietal Denomination: VEAZ0043

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,463

(22) Filed: Jun. 12, 2017

(65) Prior Publication Data

US 2018/0084692 P1 Mar. 22, 2018

(51) Int. Cl.
*A01H 5/02* (2018.01)

(52) U.S. Cl.
USPC ..... Plt./308
CPC ..... *A01H 5/02* (2013.01)

(58) Field of Classification Search
USPC ..... Plt./308
See application file for complete search history.

(56) References Cited

PUBLICATIONS

PLUTO Plant Classification Database Mar. 8, 2018. p. 1.*

* cited by examiner

*Primary Examiner* — Annette H Para
(74) *Attorney, Agent, or Firm* — Dale Skalla

(57) ABSTRACT

A new *Verbena* plant named 'VEAZ0043' particularly distinguished by bi-colored, lilac and lavender very large-sized flowers, large inflorescences, deep green foliage, strong jasmine-like scent and an upright plant habit.

1 Drawing Sheet

Latin name of the genus and species of the plant claimed: *Verbena hybrida.*

Varietal denomination: 'VEAZ0043'.

BACKGROUND OF THE NEW PLANT

The present invention comprises a new *Verbena*, botanically known as *Verbena hybrida*, and hereinafter referred to by the variety name 'VEAZ0043'.

'VEAZ0043' is a product of a planned breeding program. The new cultivar has bi-colored, lilac and lavender very large-sized flowers, large inflorescences, deep green foliage, strong jasmine-like scent and an upright plant habit.

'VEAZ0043' originated from a hybridization made in August 2012 in a greenhouse in Enkhuizen, The Netherlands.

The female parent was an unpatented proprietary plant designated 'R1462-1' with purple and white flower color and an upright and compact plant habit. This has no scent and smaller flowers.

The male parent of 'VEAZ0043' is unknown because it was a cloud of all the plants in the field.

The seed was sown in February 2013 in a greenhouse in Enkhuizen, The Netherlands. 'VEAZ0043' was selected as one flowering plant within the progeny of the stated cross in the August 2013.

The first act of asexual reproduction of 'VEAZ0043' was accomplished when vegetative cuttings were propagated from the initial selection in August 2013 in a greenhouse in Enkhuizen, The Netherlands.

BRIEF SUMMARY OF INVENTION

Horticultural examination of plants grown from cuttings of the plant initiated in August 2013, and continuing thereafter, has demonstrated that the combination of characteristics as herein disclosed for 'VEAZ0043' are firmly fixed and are retained through successive generations of asexual reproduction.

'VEAZ0043' has not been observed under all possible environmental conditions. The phenotype may vary significantly with variations in environment such as temperature, light intensity, and day length.

A Plant Breeder's Right for this cultivar was applied for in the European Union on Sep. 20, 2016, No. 2016/2279. 'VEAZ0043' has not been made publicly available prior to the effective filing date of this application, notwithstanding any disclosure that may have been made less than one year prior to the effective filing date of this application by the inventor or another who obtained 'VEAZ0043' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0043' with colors being as true as possible with an illustration of this type.

Figure 1:
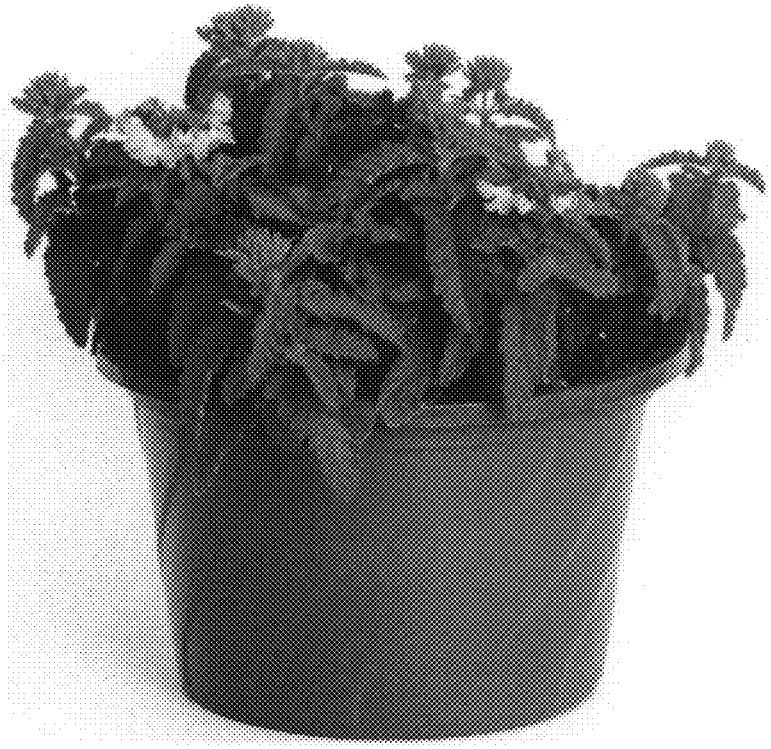
Figure 2:
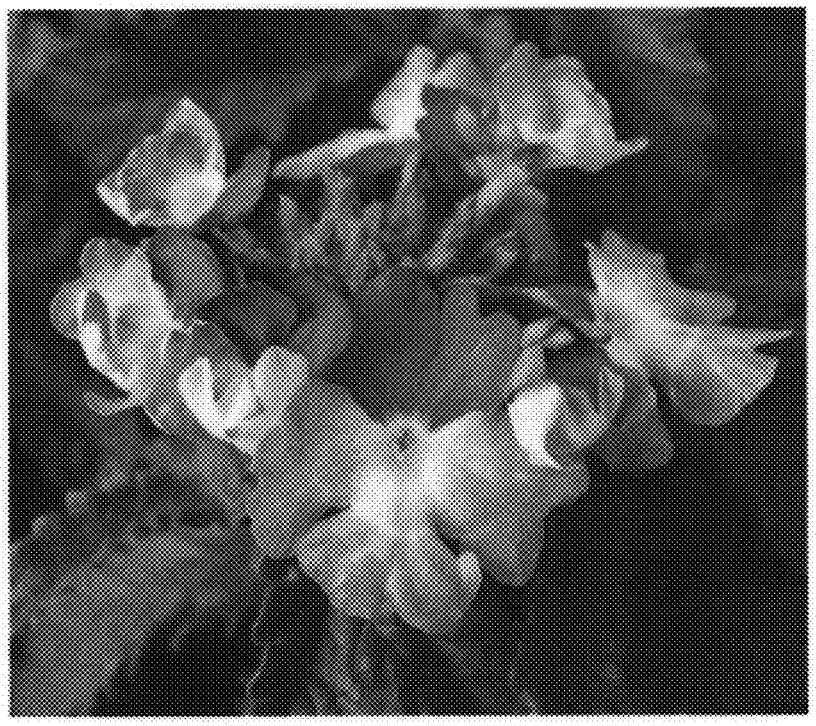

The photographic drawing in FIG. 1 shows three flowering plants of the new variety in a hanging-basket, and in FIG. 2 a close-up of the inflorescence.

DETAILED BOTANICAL DESCRIPTION

The plant descriptions and measurements were taken in Andijk, The Netherlands on Apr. 28, 2017 indoors in natural light. The plants used were about 8 weeks of age, growing in a 23 cm hanging basket, 3 plants each, in a greenhouse.

The aforementioned photographs were taken in Gilroy, Calif., USA, as described.

Color references are made to The Royal Horticultural Society Colour Chart (R.H.S.) 2001.

TABLE 1

DIFFERENCES BETWEEN THE NEW VARIETY 'VEAZ0043' AND A MOST SIMILAR VARIETY

| | 'VEAZ0043' | 'Wicked Cool Blue' |
|---|---|---|
| Flower size: | Large | Smaller |
| Plant habit: | Upright | Semi-trailing |
| Floriferoussness: | Good | Medium |

Plant:

*Form, growth and habit.*—Herbaceous, upright vigorous and free-branching.

*Plant height.*—17.0 cm.

*Plant height (inflorescence included).*—23.0 cm.

*Plant width.*—30.0 cm.

Roots:

*Number of days to initiate and produce roots.*—10-14 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 138A.

*Immature, leaf color, lower surface.*—RHS 137B.

*Mature, leaf color, upper surface.*—RHS 137A.

*Mature, leaf color, lower surface.*—RHS 137B.

*Length.*—4.2 cm.

*Width.*—2.9 cm.

*Shape.*—Ovate.

*Base shape.*—Cordate.

*Apex shape.*—Acute.

*Margin.*—Divided, sinuate.

*Texture, upper surface.*—Densely pubescent.

*Lower surface.*—Canescent; glandular hairs.

*Color of veins, upper surface.*—RHS 144A.

*Color of veins, lower surface.*—RHS 147C.

*Pattern of veining.*—Pinnate.

*Petiole, color.*—RHS 147C.

*Petiole, length.*—0.5 cm.

*Petiole, width.*—0.15 cm.

*Texture.*—Hirsute; glandular hairs.

Stem:

*Branching characteristics.*—Potentially at every node.

*Quantity of main branches per plant.*—About 12.

*Color of stem.*—RHS 143C.

*Stem length.*—15-19 cm.

*Stem width.*—0.3 cm.

*Length of internodes.*—2-3.5 cm.

*Texture.*—Canescent.

*Color of peduncle.*—RHS 144B.

*Length of peduncle.*—4.5 to 6.2 cm.

*Peduncle diameter.*—0.2 cm.

*Texture.*—Canescent.

Inflorescence:

*Type.*—Umbel-like, but actually a spike, umbrella-shaped to nearly semi-spherical.

*Blooming habit.*—Continuously flowering through the summer months.

*Lastingness of individual blooms on the plant.*—About 4 days in the greenhouse.

*Fragrance.*—Strong, sweet like Jasmine.

*Number of inflorescences per plant.*—About 36 at various stages.

*Horizontal diameter of inflorescence.*—About 6.6 cm.

*Depth of inflorescence.*—4.6 cm.

*Number of florets per inflorescence (including any buds at the time).*—26.

Bud (just when opening/showing color):

*Color.*—RHS 79D, purple, with RHS 149D.

*Length.*—0.4 cm.

*Width.*—0.3 cm.

*Shape.*—Tubular with bulbous apex.

Floret:

*Form.*—Sessile; salverform, composed of 5 partly fused petals with a base of a narrow tube.

*Immature color, 2 top petals, upper surface.*—RHS N81A with RHS N87B shades, and a small white ring around the center.

*Immature color, 2 top petals, lower surface.*—RHS N87D.

*Immature color, 3 lower petals, upper surface.*—RHS 86C, with a small white eye RHS 155D.

*Immature color, 3 lower petals, lower surface.*—White, RHS 157D.

*Mature color, 2 top petals, upper surface.*—RHS N87C with RHS N87B shades, and a small white ring around the center.

*Mature color, 2 top petals, lower surface.*—RHS N87D.

*Mature color, 3 lower petals, upper surface.*—RHS 86D with a small white eye RHS 155D.

*Mature color, 3 lower petals, lower surface.*—White, RHS 155B.

*Floret diameter.*—2.9 cm.

*Floret length (depth).*—2.8 cm.

*Petal length.*—1.7 cm.

*Petal width.*—1.1 cm.

*Shape.*—Obcordate.

*Apex shape.*—Emarginate.

*Margin.*—Entire.

*Petal texture, upper surface.*—Papillose.

*Petal texture, lower surface.*—Glabrous.

*Corolla tube length.*—1.6 cm.

*Corolla tube width.*—0.15 cm.

*Corolla tube color inside.*—RHS 150D.

*Tube color outside.*—RHS 150D to RHS 145D at floret base.

*Corolla texture, inside.*—Papillose, long white hairs and short hairs.

*Corolla texture, outside.*—Glabrous.

*Throat hair color.*—RHS 155D but whiter.

Calyx:

*Type.*—Five sepals whose margins are fused to each other along their length, with a transparent membrane of less than 0.1 cm in width, and with one smaller sepal attached to the base of the calyx.

*Color of sepals.*—RHS 143B.

*Length of sepals.*—1.2 cm.

*Width of sepals.*—0.2 cm.

*Sepal shape.*—Fused, linear.

*Apex shape.*—Acute.

*Margins.*—Entire.

*Texture.*—Densely covered with short hair, also glandular hairs.

Reproductive organs:

*Gynoecium.*—

*Pistil.*—1.

*Pistil length.*—1.5 cm.

*Style color.*—RHS N144D.

*Style length.*—1.4 cm.

*Stigma color.*—RHS 144A.

*Ovary color.*—RHS 144B.

*Ovary length.*—0.2 cm.

*Ovary width.*—0.1 cm.

*Androecium.*—

*Stamens.*—Anthers and filaments fused to upper half of corolla tube; four anthers with two pollen sacs per anther.

*Color of filaments.*—RHS 151D.

*Filament length.*—0.1 cm.

*Anther color.*—RHS 151D.

*Anther length.*—0.1 cm.

*Pollen amount.*—Little.

*Pollen color.*—RHS 1B.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0043' substantially as illustrated and described herein.

* * * * *